United States Patent [19]

Sirvin

[11] Patent Number: 5,185,775
[45] Date of Patent: Feb. 9, 1993

[54] X-RAY APPARATUS INCLUDING A HOMOGENIZING FILTER

[75] Inventor: Pierre Sirvin, Ville d'Avray, France

[73] Assignee: General Electric CGR S.A., Issy les Moulineaux, France

[21] Appl. No.: 608,347

[22] Filed: Nov. 2, 1990

[30] Foreign Application Priority Data

Nov. 24, 1989 [FR] France ................... 89 15510

[51] Int. Cl.$^5$ ............................. G21K 3/00
[52] U.S. Cl. ................... 378/156; 378/146; 378/159
[58] Field of Search ............ 378/145, 146, 156–159, 378/62

[56] References Cited

U.S. PATENT DOCUMENTS

| 2,630,536 | 3/1953  | Vladeff ............... 378/159 |
| 3,660,664 | 5/1972  | Pasmeg ............... 378/159 |
| 3,755,672 | 8/1973  | Edholm et al. . |
| 4,286,167 | 8/1981  | La Riviere . |
| 4,715,056 | 12/1987 | Vlasbloem et al. ........ 378/146 |
| 4,947,416 | 8/1990  | McFaul et al. ........... 378/146 |
| 4,953,189 | 8/1990  | Wang ................ 378/146 |
| 4,953,192 | 8/1990  | Plewes ................ 378/146 |
| 4,972,458 | 11/1990 | Plewes ................ 378/146 |

FOREIGN PATENT DOCUMENTS

| 146992   | 7/1985  | European Pat. Off. . |
| 1079448  | 4/1960  | Fed. Rep. of Germany ...... 378/159 |
| 3017745  | 11/1980 | Fed. Rep. of Germany . |
| 2485790  | 12/1981 | France . |

Primary Examiner—David P. Porta
Attorney, Agent, or Firm—Cushman, Darby & Cushman

[57] ABSTRACT

The invention applies to radiological apparatuses for angiographic examination. The invention lies in the fact that an X-ray attenuation filter is disposed between the X-ray source and the patient, said filter introducing attenuation on the path of each X-ray such that the total attenuation to which each X-ray is subjected on its path to the receiver is substantially the same for all of the paths in the X-ray beam, thereby homogenizing the exposure of the image-forming receiver.

10 Claims, 1 Drawing Sheet

X-RAY APPARATUS INCLUDING A HOMOGENIZING FILTER

BACKGROUND OF THE INVENTION

1. Field of the Invention

The present invention relates to X-ray apparatuses, and more particularly, within such apparatuses, it relates to a device or filter for spatially modifying exposure to X-rays as a function of the morphology of the patient's body or of the portion of the body receiving X-rays.

2. Description of the Prior Art

The invention is more particularly intended for X-ray apparatuses that are used for angiographical examination of the lower limbs. It is recalled that angiography is the application and adaptation of the radiological technique to the vascular network: arteries, veins, tissues under perfusion. It makes use of "contrast" liquids based on iodine which are opaque to X-rays and which are injected into the vascular network in order to enable it to be visualized by distinguishing it from the surrounding tissue. More precisely, the patient is laid on a table which is designed to move relative to a source of radiation associated with a receiver disposed on the other side of the patient from the source. The practitioner injects the X-ray opaque liquid, known as the "contrast" liquid, into an artery or a vein of the patient lying on the table. Then, a few seconds after the injection, a plurality of successive X-ray pictures of the patient are taken so as to visualize and measure the progress of the contrast substance along the blood vessels as a function of time.

When angiographic examination is applied to the lower limbs, i.e. over a length of about 120 centimeters, several methods are currently in use.

The first method consists in using an "arteriophlebograph" as the receiver equipment, which equipment comprises a hexagonal drum with six film and reinforcing screen pairs provided thereon, each pair being 120 cm long and 35 cm wide, thereby enabling six exposures and thus six photographic pictures to be obtained at different instants. In this method, each picture provides an image over the full length of the limbs and the patient therefore receives a considerable dose of X-rays since the entire lower portion of the body is exposed when each picture is taken. In addition, since the exposure is the same over the entire lower portion of the body, there is a large difference in contrast between the abdomen and the feet, given the differences in X-ray absorption presented by these portions of the body. This large difference in contrast makes it difficult to identify the contrast substance. In order to reduce this contrast difference, proposals have been made to place a rudimentary filter on the path of the X-ray beams, the filter being of the wedge type, i.e. being constituted by a sheet of varying thickness, thereby attenuating X-rays at the feet more than at the abdomen. Proposals have also been made to use a reinforcing screen whose X-ray to light photon efficiency varies over the length of the lower limbs, so as to present low efficiency at the feet and medium to high efficiency at the abdomen. The changes in contrast that are obtained using such devices, i.e. a wedge-shaped plate or a varying efficiency reinforcing screen, are fairly coarse.

A second method consists in examining the lower limbs zone by zone, with each zone corresponding, for example, to an effective field of 35 cm×35 cm or to a diameter of 30 cm or of 35 cm. To do this, relative displacement is obtained between the X-ray beam and the patient between taking successive pictures such that each picture gives a partial image of the limbs, and the resulting set of images covers the entire length of the limbs.

In this second method, the exposure parameters vary from one picture to the next in order to take into account of the variations in thickness between the abdomen and the feet. In practice, given the dynamic range of the variations required, it is necessary to vary both the supply voltage kV applied to the tube of the X-ray source and the product mA.s of the anode current mA multiplied by the exposure time s. This therefore results in a change in the contrast between the images taken of different zones of the patient, and this makes identifying the contrast substance difficult, and more generally makes analyzing the images difficult, particularly if they are processed digitally.

In both methods outlined briefly above, some portions of the sensitive surface of the receiver, corresponding to the gap between the legs or to margins outside the legs are subjected to X-rays which are unattenuated and this degrades image quality. This problem is solved by placing various absorbent bodies such as plastic cylinders filled with water around the patient and between the patient's legs. Manipulating such cylinders is inconvenient both for the patient and for the practitioner.

The object of the present invention is therefore to provide an X-ray apparatus which avoids the above-mentioned drawbacks. This result is achieved by using a filtering or absorption device which is disposed between the source of radiation and the receiver, and preferably in the vicinity of the source.

SUMMARY OF THE INVENTION

The present invention provides a radiological apparatus, in particular for radiological examination of the lower limbs, the apparatus comprising an X-ray source which emits a beam of X-rays towards a patient, a table on which the patient may be laid out, and an X-ray receiver disposed on the opposite side of the table to the side on which the source is placed, the table and/or the source-receiver pair being capable of displacement relative to each other so that the X-ray beam is capable at least of scanning the lower limbs of the patient in the longitudinal direction, said apparatus further including an X-ray attenuation filter device which is disposed between the X-ray source and the receiver, the said device providing attenuation on each X-ray path in the beam such that the total attenuation to which the X-rays are subjected on any of the paths to the receiver is substantially the same for all of the paths in the beam, thereby homogenizing the exposure of the image-forming receiver. Preferably, the filter is disposed close to the source of radiation and first means are provided to displace the filter perpendicularly relative to the beam in such a manner that the said beam intersects corresponding portions of the filter and of the patient's body.

According to another feature of the invention, second means are provided to modify the ratio between the source-filter distance and/or the filter-patient distance in such a manner as to adapt the size of the filter to the size of the patient.

According to another feature of the invention, third means are provided for displacing the filter horizontally over a distance which is different from the advance step size defined by the scale factor relating the size of the patient to the length of the filter.

According to another feature of the invention, provision is made for using a plurality of interchangeable filters, with each filter being adapted to the morphology of the patient to be examined.

BRIEF DESCRIPTION OF THE DRAWINGS

Other features and advantages of the present invention appear from reading the following description of a particular embodiment, said description being made with reference to the accompanying drawing in which.

DETAILED DESCRIPTION OF THE INVENTION

Figure 1:
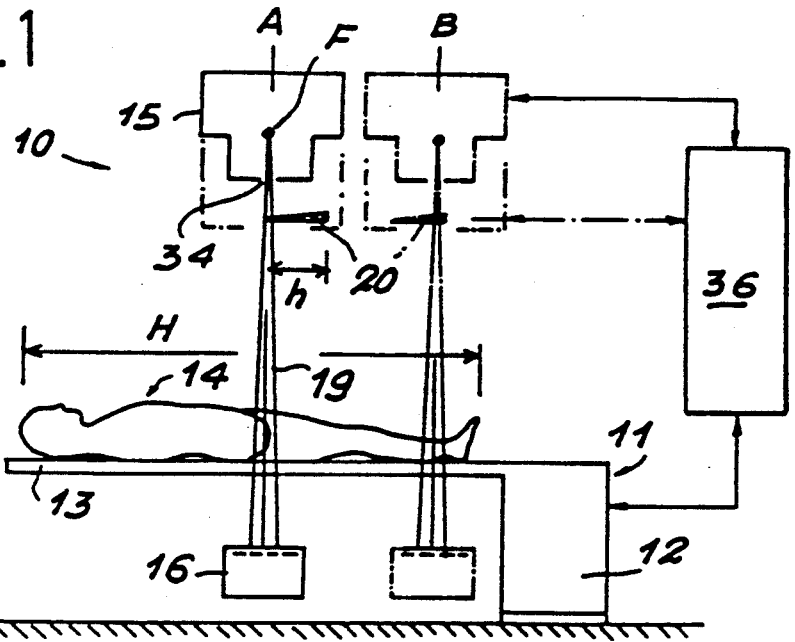
FIG. 1 is a diagram of a radiological apparatus for angiographic examination and including a homogenizing filter according to the present invention.

A radiological apparatus 10 for angiographic examination schematically comprises (FIG. 1) a table 11 having a base 12 with a sliding panel 13 mounted thereon to support a patient 14.

The patient 14 is irradiated by a beam 19 of X-rays which is emitted by a radiation source 15 having a focus F and an aperture 34. After being absorbed to a greater or lesser extent by the patient's body, the X-rays are detected by a receiver 16 which may be any conventional receiver such as photographic film, a screen in combination with photographic film, or an image intensifier. If an image intensifier is used, then the light signals delivered by the image intensifier are processed in conventional manner in order to obtain images suitable for tracking the progress of the contrast substance.

Figure 2:
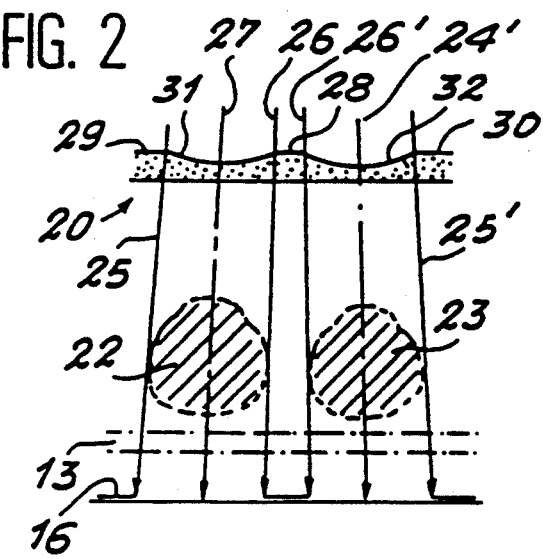
FIG. 2 is a diagram showing the proportionality relationships which are used for making a homogenizing filter according to the invention.

In order to track the progress of the contrast substance, the X-ray beam 19 needs to be displaced relative to the patient 14, either by displacing the source 15 as shown in FIG. 1, or else by sliding the panel 13. In this figure, means for controlling the displacement of the source 15 and of the receiver 16 are represented by a device 36. This device 36 is a computer which receives position data relating to the source 15 and to the table 11 and which issues instructions for displacing the source 15 and the table 11, both of which are fitted with motorized horizontal displacement means (not shown in FIG. 1). As shown in FIGS. 2 and 3, the X-rays are subject to very different degrees of attenuation since they go through portions of the patient's body having a wide range of thicknesses and/or having different absorption coefficients. Thus, the abdomen attenuates X-rays more than do the legs because of the difference in thickness, but even so the bones in the legs also attenuate strongly because they have a higher coefficient of absorption than do the tissues of the abdomen. In addition, between the legs and around the margins of the legs and the abdomen, the X-rays are not attenuated.

These phenomena lead to images having very high degrees of contrast, making them difficult to analyze or else obliging the practitioner to change the exposure parameters.

In order to mitigate these drawbacks, the invention proposes interposing a "homogenizing" filter between the X-ray source and the receiver, and preferably between the source and the patient and in the proximity of the source.

The filter 20 is constituted by a plate 27 which is made of an X-ray absorbent material and which is of varying thickness so as to attenuate each X-ray path in such a manner that the total attenuation to which the said X-rays are subjected over their entire path all the way to the receiver is substantially the same for all paths in the X-ray beam. As a result, maximum attenuation is inserted between the legs and minimum attenuation is inserted for the abdomen zone, and the attenuation in other zones has intermediate values. An image is then obtained in which the exposure is homogenized.

Perfect compensation would lead to an image that was uniformly gray on which only the contrast substance conveyed by the blood vessels would appear. The geometrical diagrams of FIGS. 2 and 3 serve to explain how the thickness of the filter is determined for each X-ray path, taking account of the respective positions of the filter 20 and of the patient 14 relative to the focus F of the X-ray source 15, which positions define a scale factor. This scale factor is used for calculating the lateral and transverse dimensions of the filter, and the nearer the filter is to the focus F, the smaller these dimensions. In FIG. 2, which corresponds to a section through the knees of the patient, the rays 26 and 26' determine the limits of the gap between the legs and define the high attenuation (or high thickness) central zone 28 of the filter. The rays 25 and 25' determine the side edges of the patient and define the outer high attenuation (or thickness) zones 29 and 30 of the filter. Finally, all of the rays such as 24 and 24' are attenuated by respective ones of the legs 22 and 23 of the patient and define zones 31 and 32 of varying attenuation (or thickness).

Figure 3A:
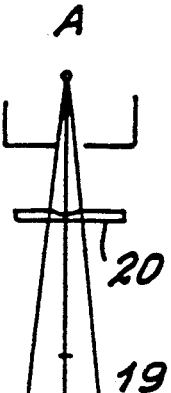
FIGS. 3a and 3b are diagrams analogous to FIG. 2 but corresponding to different positions of the X-ray beam relative to the lower limbs.
Figure 3B:
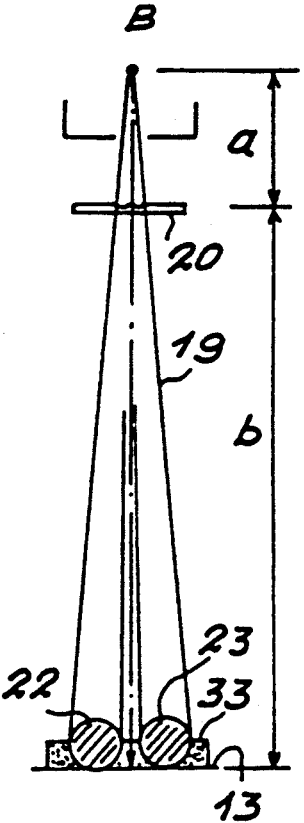
Figure 4:
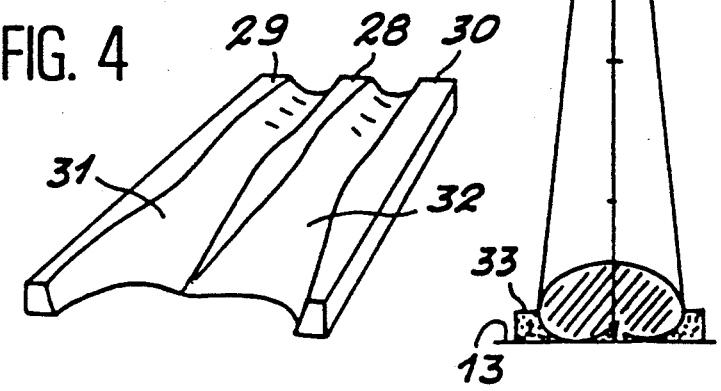
FIG. 4 is an isometric perspective view of a homogenizing filter of the present invention.

In general, the thickness of the plate 27 is selected so as to impart attenuation on the path of each X-ray such that the total attenuation to which the X-ray is subjected on its path all the way to the receiver 16 is substantially the same for all of the paths in the beam. In FIGS. 3a and 3b, which are schematic sections through the apparatus of FIG. 1 at respective positions A and B of the source and receiver pair (the receiver not being shown), the filter is shown having the shape that it would have were it to be placed level with the patient: i.e. a half-mold 33 of the lower limbs of the patient.

According to the invention, the filter is placed close to the focus F at the outlet from the source 15, thereby, as shown in FIG. 3, defining a scale factor of five between the lateral and transverse dimensions of the half-mold 33 and the corresponding dimensions of the filter 20. The thickness of the filter does not depend on the scale factor, but on the attenuation to which the X-rays are subjected passing through the patient and on the attenuation coefficient of the material used for making the filter.

Since the radiological apparatus 10 is designed to take several pictures of the lower limbs, with each picture corresponding to a different zone, the filter 20 must be capable of being displaced horizontally relative to the X-ray source 15 in order to ensure that corresponding zones of the filter and of the patient lie on the paths of the X-rays. To this end, the filter 20 is carried by the X-ray source 15 in such a manner as to be capable of sliding relative to the aperture 34 through the diaphragm of the source. In FIG. 1, the device for horizontally displacing the filter 20 is not shown, but it is clear that it can be implemented in various different ways without requiring invention. Thus, the filter may be motorized and controlled synchronously with the horizontal displacement of the source-receiver pair or of the panel 13 if the radiological apparatus is of the type in which the patient is displaced. In FIG. 1, the means for controlling horizontal displacement of the filter constitute a portion of the device 36, but the motorized displacement means are not shown.

According to the invention, the device 36 is also provided to control vertical displacement of the filter 20 and/or of the source 15 and/or of the panel 13 in such a manner as to vary the scale factor $K=(a+b)/a$, thereby adapting the filter to the size of the patient. These vertical displacement means are not shown in FIG. 1.

In addition, the device 36 is designed to adapt the horizontal displacement of the filter as a function of the scale factor $K$ and of the ratio $K'=H/h$ between the size H of the patient and the length h of the filter. It should be observed that $K=K'$ for a filter designed to correspond to the standard patient, and the filter is displaced by $h/K$ between taking two pictures so as to obtain a displacement of $H/K$ at the patient. If, in order to match the filter to the size H1 of the patient, K is changed to become K1, then it is necessary also to change the length of the horizontal displacement of the filter before taking two pictures so as to maintain correspondence in each picture between corresponding portions of the filter and of the patient. This change in displacement is determined by the device 36.

The filter must match the morphology of the patient, and according to the invention it is proposed that a plurality of filters should be made depending on whether the patient is male or female, and depending on whether the patient is large, medium, or small in size, or possibly depending on the weight of the patient. The practitioner will thus have a set of filters available from which the filter most closely matching the patient to be examined will be selected.

The filter of the invention thus makes it possible to homogenize image exposure, and consequently to distinguish the contrast substance more clearly. In addition, there is no need to change exposure parameters from one image to the next. Finally, the dynamic range of such a homogenized image is reduced, thereby making digital encoding possible without losing information. This gives rise to better digital processing of the image. The invention has been described with the filter placed at the outlet from the X-ray source, however it would be preferable to integrate the filter in the assembly constituted by the X-ray tube and the collimator including an iris and/or flaps. The material from which the filter of the invention is made may be an acrylic resin, for example, having a lead filler, e.g. the substance sold under the name "Kyowa Glass".

The varying attenuation of the filter is obtained by the varying thickness of the plate 27, but it would also be possible to vary attenuation by varying the composition of the plate materiel, e.g. by adding more highly absorbent particles, particularly for the paths between the legs and for the outside margins.

The horizontal and vertical displacement means for the source 15, the filter 20, and the table 11 are not shown in FIG. 1 so as to avoid overcrowding the figure. In any case, these means are known to the person skilled in the art and may be implemented without requiring any invention.

What is claimed is:

1. A radiological apparatus, used in radiological examination of the lower limbs, the apparatus comprising:
   an X-ray source which emits a beam of X-rays towards a patient;
   a table on which the patient may be laid out; and
   an X-ray receiver disposed on the opposite side of the table to the side on which the source is placed, the table and/or the source-receiver pair being capable of displacement relative to each other so that the X-ray beam is capable at least of scanning the lower limbs of the patient in the longitudinal direction,
   wherein said apparatus further includes a variable X-ray attenuation filter which is disposed between the X-ray source and the receiver, said filter providing attenuation on each X-ray path in the beam such that the total attenuation to which the X-rays are subjected on any of the paths to the receiver is substantially the same for all of the paths in the beam, thereby homogenizing the exposure of the image-forming receiver, and
   means for changing the scale factor $K=(a+b)/a$ between the source-patient distance $(a+b)$ and the source-to-filter distance a in such a manner as to adapt said filter to the size of the patient.

2. Radiological apparatus according to claim 1, wherein said filter is associated with means for displacing it perpendicularly relative to an X-ray beam to ensure that said beam intersects corresponding portions of said filter and of the patient's body.

3. Radiological apparatus according to claim 1 wherein said filter is disposed in the proximity of the source and wherein means for displacing said filter are fixed to said source.

4. A radiological apparatus, used in radiological examination of the lower limbs, the apparatus comprising:
   an X-ray source which emits a beam of X-rays towards a patient,
   a table on which the patient may be laid out;
   and an X-ray receiver disposed on the opposite side of the table to the side on which the source is placed, the table and/or the source-receiver pair being capable of displacement relative to each other so that the X-ray beam is capable at least of scanning the lower limbs of the patient in the longitudinal direction,
   wherein said apparatus further includes a variable X-ray attenuation filter device which is disposed between the X-ray source and the receiver, said filter device providing attenuation on each X-ray path in the beam such that the total attenuation to which the X-rays are subjected on any of the paths to the receiver is substantially the same for all of the paths in the beam, thereby homogenizing the exposure of the image-forming receiver, and
   wherein said filter device includes a plurality of interchangeable filters are provided, each filter being adapted to a type of patient morphology.

5. Radiological apparatus according to claim 4, wherein said filter device is associated with means for displacing it perpendicularly relative to an X-ray beam to ensure that said beam intersects corresponding portions of said filters and of the patient's body.

6. Radiological apparatus according to claim 4 wherein said varying attenuation of the filter device is obtained by varying thickness of the material constituting said filters.

7. Radiological apparatus according to claim 4 wherein said filter device is disposed in the proximity of the source and wherein means for displacing said filter device are fixed to said source.

8. A radiological apparatus, used in radiological examination of the lower limbs, the apparatus comprising:
   an X-ray source which emits a beam of X-rays towards a patient;
   a table on which the patient may be laid out;
   and an X-ray receiver disposed on the opposite side of the table to the side on which the source is placed, the table and/or the source-receiver pair being capable of displacement relative to each other so that the X-ray beam is capable at least of scanning the lower limbs of the patient in the longitudinal direction,
   wherein said apparatus further includes a variable X-ray attenuation filter which is disposed between the X-ray source and the receiver, said filter providing attenuation on each X-ray path in the beam such that the total attenuation to which the X-rays are subjected on any of the paths to the receiver is substantially the same for all of the paths in the beam, thereby homogenizing the exposure of the image-forming receiver, and
   whereby the varying attenuation of said filter is obtained by varying the composition of the material constituting said filter.

9. Radiological apparatus according to claim 8, wherein said filter is associated with means for displacing it perpendicularly relative to an X-ray beam to ensure that said beam intersects corresponding portions of said filter and of the patient's body.

10. Radiological apparatus according to claim 8 wherein said filter is disposed in the proximity of the source and wherein means for displacing said filter are fixed to said source.

* * * * *